United States Patent [19]

Hirose et al.

[11] Patent Number: 5,286,695

[45] Date of Patent: Feb. 15, 1994

[54] OLIGOMERIZATION CATALYST FOR α-OLEFINS AND PROCESS FOR OLIGOMERIZING α-OLEFINS

[75] Inventors: Keiji Hirose, Yamaguchi, Japan; Wilhelm Keim, Aachen, Fed. Rep. of Germany

[73] Assignee: Mitsui Petrochemical Industries, Ltd., Tokyo, Japan

[21] Appl. No.: 936,275

[22] Filed: Aug. 28, 1992

[30] Foreign Application Priority Data

Sep. 5, 1991 [JP] Japan .................................. 3-226166

[51] Int. Cl.$^5$ ............................................ B01J 31/00
[52] U.S. Cl. ................................... 502/117; 502/121; 585/513; 585/514
[58] Field of Search ................ 502/117, 121; 585/513, 585/514

[56] References Cited

U.S. PATENT DOCUMENTS 3,485,892 12/1969 Griffin, Jr. et al. ............ 260/683.15
4,155,946 5/1979 Sato et al. ..................... 585/513

FOREIGN PATENT DOCUMENTS 0091232 10/1983 European Pat. Off. .
1810027 12/1967 Fed. Rep. of Germany .
2395976 1/1979 France .
19408 4/1987 Japan .

*Primary Examiner*—Anthony McFarlane
*Assistant Examiner*—Nhat D. Phan
*Attorney, Agent, or Firm*—Sherman and Shalloway

[57] ABSTRACT

An oligomerization catalyst for α-olefins, comprising

[A] at least one nickel compound selected from the group consisting of a nickel salt of organic acid, a nickel salt of inorganic acid and a complex compound of nickel;

[B] an organoaluminum oxy-compound having at least 3 aluminum atoms in the molecule; and

[C] a trivalent phosphorous compound represented by the general formula $PR^1R^2R^3$ wherein $R^1$ to $R^3$ are each independently a hydrocarbon group or substituted hydrocarbon group of 1 to 10 carbon atoms.

A process for oligomerizing α-olefin, wherein α-olefin is oligomerized in the presence of the catalyst mentioned above.

12 Claims, No Drawings

OLIGOMERIZATION CATALYST FOR α-OLEFINS AND PROCESS FOR OLIGOMERIZING α-OLEFINS

FIELD OF THE INVENTION

The present invention relates to an oligomerization catalyst for α-olefins and a process for oligomerizing α-olefins using the oligomerization catalyst. The present invention relates more in detail to an oligomerization catalyst having high activity and capable of producing a specific product and a process for oligomerizing α-olefins using the catalyst.

BACKGROUND OF THE INVENTION

Of oligomerization catalysts for α-olefins, many of the dimerization catalysts for α-olefins include a transition metal as an activity center thereof. The known dimerization catalysts include a catalyst system comprising a transition metal compound and an organoaluminum compound, a transition metal compound catalyst and a transition metal heterogeneous catalyst. Of these dimerization catalysts, the catalyst system comprising a transition metal compound and an organoaluminum compound is excellent in both catalytic activity an dimer yield.

A catalyst comprising a nickel compound and an organoaluminum compound is known as the dimerization catalyst comprising a transition metal compound and an organoaluminum compound. For example, Japanese Patent Publn. No. 19408/1987 discloses a process for dimerizing lower α-olefins, wherein there is used a catalyst comprising (A) a nickel compound, (B) a bis(-dialkylaluminoxane) represented by a formula $(R_2Al)_2O$ (wherein R is alkyl of 1 to 6 carbon atoms or cycloalkyl), (C) a phosphorus-containing compound, and (D) a halogenated phenolic compound. However, catalysts capable of selectively forming both an α-olefin dimer and an α-olefin trimer were not known.

The present inventors have conducted intensive research in order to obtain a catalyst having high activity compared with conventional dimerization catalysts for α-olefins, and capable of producing specific dimers in a high yield and in a high selection ratio. As a result, the present inventors have found that a catalyst comprising at least one nickel compound selected from the group consisting of nickel salts of organic acids, nickel salts of inorganic acids and complex compounds of nickel, an organoaluminum oxy-compound having at least 3 aluminum atoms in the molecule and a trivalent phosphorous compound is excellent in catalyst activity, a dimerization yield and selectivity of the products. The present inventors have still further found that when ethene is used as α-olefin, such a catalyst as described above is capable of producing a trimer of ethene. The present invention has been achieved based on the finding described above.

OBJECT OF THE INVENTION

An object of the present invention is to provide an oligomerization catalyst for α-olefins having high activity and capable of producing a specific product in a high selectivity. Another object of the invention is to provide a process for oligomerizing α-olefins using such a catalyst.

SUMMARY OF THE INVENTION

An oligomerization catalyst for α-olefin according to the present invention comprises

[A] at least one nickel compound selected from the group consisting of a nickel salt of organic acid, a nickel salt of inorganic acid and a complex compound of nickel,

[B] an organoaluminum oxy-compound having at least 3 aluminum atoms in the molecule, and

[C] a trivalent phosphorous compound represented by the formula [I]

$$PR^1R^2R^3 \qquad [I]$$

wherein $R^1$, $R^2$ and $R^3$ are each independently a hydrocarbon group or substituted hydrocarbon group having 1 to 10 carbon atoms.

A process for oligomerizing α-olefin according to the present invention comprises oligomerizing α-olefin in the presence of the catalyst as described above.

DETAILED DESCRIPTION OF THE INVENTION

The oligomerization catalyst for α-olefins according to the present invention and the process for oligomerizing α-olefins using the catalyst are concretely illustrated hereinafter.

The catalyst component [A] used in the invention is at least one nickel compound selected from the group consisting of a nickel salt of organic acid, nickel salt of inorganic acid and a complex compound of nickel.

Concrete examples of the nickel salt of organic acid include nickel naphthenate, nickel formate, nickel acetate, nickel benzoate and nickel oxalate.

Concrete examples of the nickel salt of inorganic acids include nickel chloride, nickel bromide, nickel iodide, nickel fluoride, nickel nitrate, nickel sulfate, nickel hydroxide and nickel oxide.

Concrete examples of the complex compound of nickel include bis(acetylacetonato)nickel, bis(ethyl acetoacetonate)nickel, bis(dimethylglioximato)nickel, bis(cyclopentadienyl)nickel, bis(cyclooctadienyl)nickel and nickel carboxyl complexes.

Of these nickel compounds mentioned above, bis(cyclooctadienyl)nickel is preferably used.

Two or more of these nickel compounds may be used in combination.

The catalyst component [B] used in the invention may be a conventionally known aluminoxane, or may also be a benzene insoluble organoaluminum oxy-compound.

The conventionally known aluminoxanes can be manufactured, for example, by the following procedures:

(1) A procedure for recovering an aluminoxane as its solution in hydrocarbon which comprises reacting an organoaluminum compound such as trialkylaluminum with a suspension in a hydrocarbon solvent of a compound having adsorbed water or a salt containing water of crystallization, for example, hydrates of magnesium chloride, copper sulfate, aluminum sulfate, nickel sulfate or cerous chloride.

(2) A procedure for recovering an aluminoxane as its solution in hydrocarbon which comprises allowing water, ice or water vapor to directly react with an organoaluminum compound such as trialkylaluminum in a solvent such as benzene, toluene, ethyl ether and tetrahydrofuran.

(3) A procedure which comprises allowing an organotin oxide such as dimethyltin oxide and dibutyltin oxide to react with an organoaluminum compound such as trialkylaluminum in a solvent such as decane, benzene and toluene.

The aluminoxane may contain a small amount of organometal components. Moreover, the solvent or the organoaluminum compound which has not reacted may be removed by distillation from the recovered solution of aluminoxane described above, and the resultant product may be redissolved in a solvent.

Concrete examples of the organoaluminum compounds used for preparing such a solution of an aluminoxane as mentioned above include trialkylaluminum such as trimethylaluminum, triethylaluminum, tripropylaluminum, triisopropylaluminum, tri-n-butylaluminum, triisobutylaluminum, tri-sec-butylaluminum, tri-tert-butylaluminum, tripentylaluminum, trihexylaluminum, trioctylaluminum, tridecylaluminum, tricyclohexylaluminum, tricyclooctylaluminum;

dialkylaluminum halides such as dimethylaluminum chloride, diethylaluminum chloride, diethylaluminum bromide and diisobutylaluminum chloride;

dialkylaluminum hydrides such as diethylaluminum hydride and diisobutylaluminum hydride;

dialkylaluminum alkoxides such as dimethylaluminum methoxide and diethylaluminum ethoxide; and dialkylaluminum aryloxides such as diethylaluminum phenoxide.

Of the organoaluminum compounds as exemplified above, trialkylaluminum is preferably used.

Furthermore, there may also be used as the organoaluminum compound isoprenylaluminum represented by the general formula [II]

$(i-C_4H_9)_xAl_y(C_5H_{10})_z$ [II]

wherein x, y and z are each a positive number, and $z \geqq 2x$.

The organoaluminum compounds mentioned above may be used either singly or in combination.

Solvents used in the solutions of aluminoxanes include aromatic hydrocarbons such as benzene, toluene, xylene, cumene and cymene; aliphatic hydrocarbons such as pentane, hexane, heptane, octane, decane, dodecane, hexadecane and octadecane; alicyclic hydrocarbons such as cyclopentane, cyclohexane, cyclooctane and methylcyclopentane; petroleum fractions such as gasoline, kerosene and gas oil; or halides, particularly chlorides and bromides, of the above-mentioned aromatic, aliphatic and alicyclic hydrocarbons. In addition thereto, there may also be used ethers such as ethyl ether and tetrahydrofuran. Of these solvents as exemplified above, particularly preferred are aromatic hydrocarbons.

The benzene-insoluble organoaluminum oxy-compound used in the invention can be prepared, for example, by bringing a solution of an aluminoxane into contact with water or an active hydrogen-containing compound.

Examples of the active hydrogen-containing compound include alcohols such as methanol, ethanol, n-propanol and isopropanol, diols such as ethylene glycol and hydroquinone, and organic acids such as acetic acid and propionic acid. Of these compounds, preferred are alcohols and diols, and particularly preferred are alcohols.

Water or the active hydrogen-containing compound with which the solution of an aluminoxane is brought into contact may be used as a solution or dispersion in a hydrocarbon solvent such as benzene, toluene and hexane, an ether solvent such as tetrahydrofuran or an amine solvent such as triethylamine, or may be used in the form of vapor or solid. The water with which the solution of aluminoxane is brought into contact may be water of crystallization of a salt such as magnesium chloride, magnesium sulfate, aluminum sulfate, copper sulfate, nickel sulfate, iron sulfate and cerous chloride, or adsorbed water absorbed to an inorganic compound such as silica, alumina and aluminum hydroxide or polymers.

The contact reaction of the solution of an aluminoxane with water or the active hydrogen-containing compound is carried out usually in a solvent, for example, in a hydrocarbon solvent.

Examples of the solvents used in this case include aromatic hydrocarbons such as benzene, toluene, xylene, cumene and cymene;

aliphatic hydrocarbons such as pentane, hexane, heptane, octane, decane, dodecane, hexadecane and octadecane; and alicyclic hydrocarbons such as cyclopentane, cyclohexane, cyclooctane and methylcyclohexane.

The examples of the solvents may also include petroleum fractions such as gasoline, kerosene and gas oil; halides, particularly chlorides and bromides, of the above-mentioned aromatic, aliphatic and alicyclic hydrocarbons; and ethers such as ethyl ether and tetrahydrofuran. Of these solvents as exemplified above, particularly preferred are aromatic hydrocarbons.

In the reaction as mentioned above, water or the active hydrogen-containing compound is used in an amount of 0.1 to 5 moles, preferably 0.2 to 3 moles, based on 1 mole of Al atoms present in the solution of an aluminoxane. The concentration in terms of aluminum atom of the aluminoxane in the reaction system is usually $1 \times 10^{-3}$–5 gram atom/liter, preferably $1 \times 10^{-2}$–3 gram atom/liter, and the concentration of water in the reaction system is usually $2 \times 10^{-4}$–5 mol/liter, preferably $2 \times 10^{-3}$–3 mol/liter.

The solution of an aluminoxane may be brought into contact with water or the active hydrogen-containing compound, for example, by the following procedures:

(1) A procedure which comprises bringing the solution of an aluminoxane into contact with a hydrocarbon solvent containing water or the active hydrogen-containing compound;

(2) A procedure which comprises blowing vapor of water or vapor of the active hydrogen-containing compound into the solution of an aluminoxane, thereby bringing the aluminoxane into contact with the vapor;

(3) A procedure which comprises bringing the solution of an aluminoxane into contact directly with water, ice or the active hydrogen-containing compound; and (4) A procedure which comprises mixing the solution of an aluminoxane with a suspension of an adsorbed water-containing compound or a water of crystallization-containing compound in hydrocarbon, or with a suspension of a compound, to which the active hydrogen-containing compound has been adsorbed, in hydrocarbon, thereby bringing the aluminoxane into contact with the adsorbed water, water of crystallization or active hydrogen-containing compound.

The solution of an aluminoxane as described above may contain other components so long as they do not exert adverse effects on the reaction of the aluminoxane with water or the active hydrogen-containing compound.

The above-mentioned contact reaction of the solution of an aluminoxane with water or the active hydrogen-containing compound is carried out usually at −50 to 150° C., preferably at 0° to 120° C. and more preferably at 20° to 100° C. The reaction time employed is usually 0.5 to 300 hours, preferably about 1 to 150 hours, though the reaction time varies largely depending upon the reaction temperature used.

The benzene-insoluble organoaluminum oxy-compounds used in the present invention contain an Al component, which dissolves in benzene at 60° C., in an amount of usually up to 10%, preferably up to 5% and especially up to 2% in terms of Al atom, and they are insoluble or sparingly soluble in benzene.

The solubility in benzene of the organoaluminum oxy-compounds is obtained by suspending in 100 ml of benzene the organoaluminum oxy-compound in an amount corresponding to 100 mg atoms in terms of Al atom, mixing the resulting suspension at 60° C. for 6 hours, hot filtering the resulting mixture with a G-5 glass filter equipped with a jacket kept at 60° C., washing four times the solid portion separated on the filter with 50 ml of benzene at 60° C., and measuring the amount (X mmol) of Al atoms present in the whole filtrate (X %).

When the benzene-insoluble organoaluminum oxy-compounds as described above are analyzed by infrared spectrophotometry (IR), a ratio ($D_{1260}/D_{1220}$) of an absorbance ($D_{1260}$) at about 1260 cm$^{-1}$ to an absorbance ($D_{1220}$) at about 1220 cm$^{-1}$ is up to 0.09, preferably up to 0.08 and especially in the range of 0.04 to 0.07.

Infrared spectrophotometric analysis of the organoaluminum oxy-compounds as referred to in the present invention is carried out in the following manner.

First, the organoaluminum oxy-compound is ground together with nujol in an agate mortar in a nitrogen box to form a paste-like mixture. Next, the paste-like sample thus obtained is put between KBr plates, and the IR spectrum is measured in a nitrogen atmosphere by means of IR-810 manufactured and sold by Nippon Bunko K. K. From the thus obtained IR spectrum, a $D_{1260}/D_{1220}$ ratio is sought. The ratio is obtained in the following manner.

(a) A line connecting a maximum point at about 1280 cm$^{-1}$ and a maximum point at about 1240 cm$^{-1}$ is taken as a base line $L_1$.

(b) A transmittance (T %) of an absorption minimum point at about 1260 cm$^{-1}$ and a transmittance ($T_0$ %) of a point of intersection formed by the base line $L_1$ and a line drawn vertically from the minimum point to the wave number axis (abscissa) are read, whereby an absorbance ($D_{1260}=\log T_0/T$) at about 1260 cm$^{-1}$ is calculated.

(c) Similarly, a line connecting maximum points at about 1280 cm$^{-1}$ and at about 1180 cm$^{-1}$ is taken as a base line $L_2$.

(d) A transmittance (T' %) of an absorption minimum point at about 1220 cm$^{-1}$ and a transmittance ($T'_0$ %) of a point of intersection formed by the base line $L_2$ and a line drawn vertically from the minimum point to the wave number axis (abscissa) are read, whereby an absorbance ($D_{1220}=\log T_0'/T'$) at about 1220 cm$^{-1}$ is calculated.

(e) From these values thus obtained, the value of $D_{1260}/D_{1220}$ is calculated.

The benzene-soluble Organoaluminum oxy-compound has the value of $D_{1260}/D_{1220}$ approximately between 0.10 and 0.13, and the benzene-insoluble organoaluminum oxy compounds distinctly differ from conventionally known benzene-soluble organoaluminum compounds on the value of $D_{1260}/D_{1220}$.

The benzene-insoluble organoaluminum oxy-compound as described above is presumed to have an alkyloxyaluminum unit (i) represented by the formula [III]

wherein $R^4$ is a hydrocarbon group of 1 to 12 carbon atoms.

In the above-mentioned formula [III], concrete examples of $R^4$ include methyl, ethyl, n-propyl, isopropyl, n-butyl, isobutyl, pentyl, hexyl, octyl, decyl, cyclohexyl and cyclooctyl. Of these hydrocarbon groups exemplified above, preferred are methyl and ethyl, and particularly preferred is methyl.

In addition to the alkyloxyaluminum unit (i) of the above formula (III), the benzene-insoluble organoaluminum oxy-compound of the invention may contain an oxyaluminum unit (ii) represented by the formula (IV)

wherein $R^5$ is a hydrocarbon group of 1 to 12 carbon atoms, an alkoxy group of 1 to 12 carbon atoms, an aryloxy group of 6 to 20 carbon atoms, a hydroxy group, halogen or hydrogen, $R^5$ and $R^4$ in the formula [III] being different from each other.

The organoaluminum oxy-compound desirably comprises the alkyloxyaluminum unit (i) in an amount of at least 30 mol %, preferably at least 50 mol % and particularly at least 70 mol %.

The organoaluminum oxy-compound [B] used in the invention has in the molecule 3 to 50 aluminum atoms, preferably 3 to 40 aluminum atoms, more preferably 3 to 35 aluminum atoms and especially 3 to 30 aluminum atoms. The average molecular weight of the organoaluminum oxy-compound [B] is at least 170, preferably 200 to 3000.

Such organoaluminum oxy-compounds as mentioned above may be used singly or in combination.

The catalyst component [C] used in the invention is a trivalent phosphorous compound represented by the general formula [I]

wherein $R^1$, $R^2$ and $R^3$ are each independently a hydrocarbon group or substituted hydrocarbon group having 1 to 10 carbon atoms.

In the above formula [I], $R^1$, $R^2$ and $R^3$ are each an alkyl group such as methyl, ethyl, propyl, isopropyl, butyl and isobutyl;

a cycloalkyl group such as cyclopentyl and cyclohexyl;

an aryl group such as phenyl and tolyl;

an aralkyl group such as benzyl and neophyl; and an alkoxy group such as methoxy, ethoxy and butoxy.

Concrete examples of the phosphorous compounds include trimethylphosphine, triethylphosphine, tri-n-propylphosphine, triisopropylphosphine, tri-n-butylphosphine, triisobutylphosphine, tri-sec-butylphosphine, tri-n-octylphosphine, tricyclopropylphosphine, tricyclohexylphosphine, triphenylphosphine, tri-p-tolylphosphine, tri-p-methoxyphosphine, tri-2,4,6-trimethylphenylphosphine, tri-p-isopropylphenylphosphine, phenyldiisopropylphosphine, ethyldiisopropylphosphine, ethyldi-tert-butylphosphine, ethyldicyclohexylphospine, methylpropylphenylphosphine, methylallylphenylphosphine, methylphenylbenzylphosphine and diisopropyl-tert-butylphosphine.

Of these phosphorous compounds, triisopropylphosphine is preferably used.

Two or more of these phosphorous compounds may be used in combination.

The oligomerization catalyst for α-olefins according to the invention can be prepared by mixing the above-mentioned catalyst components [A], [B] and [C] in an inert solvent and bringing the components [A], [B] and [C] into contact.

Though the catalyst components [A], [B] and [C] are mixed and brought into contact in an optionally selected order, they are desirably mixed and brought into contact in the order of contacting the catalyst components [A] and [C] at first and then contacting the resultant mixture and the catalyst component [B].

The catalyst components [A], [B] and [C] are mixed and brought into contact at a temperature of usually −80 to 250° C., preferably −30 to 120° C. and especially −10 to 50° C.

When the catalyst components [A], [B] and [C] are mixed and brought into contact, the molecular ratio ([A]/[B]) of the catalyst component [A] to the catalyst component [B] in terms of aluminum atom is in the range of usually 100 to 1/10000, preferably 1 to 1/1500, and the molecular ratio ([C]/[B]) of the catalyst component [C] to the catalyst component [B] in terms of aluminum atom is in the range of usually 400 to 4/10000, preferably 4 to 4/1500.

Concrete examples of the inert hydrocarbon solvents used in the preparation of the catalyst of the invention include aliphatic hydrocarbons such as propane, butane, pentane, hexane, heptane, octane, decane, dodecane and kerosene;

alicyclic hydrocarbons such as cyclopentane, cyclohexane and methylcyclopentane;

aromatic hydrocarbons such as benzene, toluene and xylene;

halogenated hydrocarbons such as ethylene chloride, chlorobenzene, dichlorobenzene and dichloromethane; and mixtures of the above-mentioned compounds.

Although the oligomerization of α-olefins according to the present invention is usually performed in an inert hydrocarbon solvent, the α-olefin itself may also be used as a solvent.

Concrete examples of the hydrocarbon solvent include the solvents used for the preparation of the catalyst as described above.

When α-olefins are oligomerized by using a catalyst as described above, the catalyst component is used in an amount of usually 0.001 to 10 mg atoms, preferably 0.01 to 1.0 mg atom in terms of nickel atom, based on 1 liter of the polymerization volume. The reaction temperature is usually −80° to 250° C., preferably −30° to 120° C.

In addition to the components as described above, the oligomerization catalyst for α-olefins of the invention may also contain other components useful for oligomerizing α-olefins, such as organoaluminum compounds.

Concrete examples of α-olefins used for the oligomerization of the invention include ethylene, propylene, 1-butene, 1-pentene, 3-methyl-1-butene, 1-hexene, 3-methyl-1-pentene, 4-methyl-1-pentene, 3,3-dimethyl-1-butene, 1-heptene, 1-octene and 1-decene.

Furthermore, in the present invention, there can be carried out co-oligomerization of α-olefins as mentioned above, for example, co-oligomerization of ethylene with propylene, propylene with 1-butene, ethylene with 1-butene, ethylene with 2-butene, ethylene with 1-pentene, ethylene with 1-hexene, propylene with 2-butene, propylene with 1-pentene, propylene with 1-hexene and 1-butene with 1-pentene.

The activity, types of products and selectivity of the oligomerization catalyst for α-olefins of the invention can be controlled by changing the types and amounts of the above-mentioned components, the reaction temperature and the reaction time.

For example, when propylene is dimerized in the presence of the catalyst according to the present invention, there can be obtained 2,3-dimethyl-1-butene in a high proportion.

Further, when ethylene is used as α-olefins, ethylene is trimerized in the presence of the catalyst according to the present invention to obtain, for example, 3-methylpentenes in a high selectivity.

EFFECT OF THE INVENTION

The oligomerization catalyst for α-olefins according to the present invention comprises at least one nickel compound selected from the group consisting of a nickel salt of organic acid, a nickel salt of inorganic acid and a complex compounds of nickel, an organoaluminum oxy-compound having at least 3 aluminum atoms in the molecule and a trivalent phosphorous compound. Accordingly, the catalyst has high activity and high selectivity for oligomerization of α-olefins. In the process for oligomerizing α-olefins according to the present invention, α-olefins are oligomerized in the presence of the catalyst as described above. The oligomerization reaction is therefore carried out with a high catalytic activity, and a specific oligomer can be obtained in a high selectivity.

The catalyst of the invention is particularly useful for the dimerization of an α-olefin having at least 3 carbon atoms, trimerization of ethylene and co-dimerization of α-olefins each having at least 2 carbon atoms.

EXAMPLE

The present invention is illustrated below with reference to examples, but it should be construed that the invention is in no way limited to those examples.

EXAMPLE 1

Bis(cyclooctadienyl)nickel in an amount of 0.025 mmol, 0.01 mmol of triisopropylphosphine and 2.50 mmols of methylaluminoxane having a molecular weight of about 900 g/mol (a product of Sherring Co., Ltd.) were mixed and brought into contact together in chlorobenzene. The resultant catalyst was placed in a 75 ml autoclave. Propylene was then introduced into the autoclave, and allowed to react with stirring at 0° C. for 3 hours.

After completion of the reaction, the pressure in the autoclave was reduced to the normal one. The reaction mixture was treated with dilute hydrochloric acid, and the organic layer was dried with anhydrous sodium sulfate. The reaction products were analyzed by gas chromatography, and the analysis results are shown in Table 1.

EXAMPLE 2

Propylene was oligomerized by repeating Example 1 except that the reaction was conducted at 50° C. The results are shown in Table 1.

EXAMPLE 3

Propylene was oligomerized by repeating Example 1 except that the reaction was conducted at 50° C for 10 hours. The results are shown in Table 1.

EXAMPLE 4

Propylene was oligomerized by repeating Example 1 except that triisopropylphosphine was used in an amount of 0.025 mmol. The results are shown in Table 1.

EXAMPLE 5

Propylene was oligomerized except that bis-(acetylacetonato)nickel was used in place of bis(cyclooctadienyl)nickel. The results are shown in Table 1.

EXAMPLE 6

Propylene was oligomerized by repeating Example 1 except that o-dichlorobenzene was used in place of chlorobenzene. The results are shown in Table 1.

EXAMPLE 7

Propylene was oligomerized by repeating Example 3 except that decane was used in place of chlorobenzene.

EXAMPLE 8

Propylene was oligomerized by repeating Example 7 except that the reaction was carried out at 0° C. The results are shown in Table 1.

EXAMPLE 9

Propylene was oligomerized by repeating Example 3 except that o-dichlorobenzene was used as a solvent in place of chlorobenzene, and that tricyclohexylphosphine was used in place of triisopropylphosphine. The results are shown in Table 1.

TABLE 1

| | Activity[1] | Conversion of Propylene (%) | Selectivity of Dimer (%) | Selectivity[2] (%) | Temperature (°C.) | Time (hr) |
|---|---|---|---|---|---|---|
| Example 1 | 19300 | 98.5 | 74.2 | 80.3 | 0 | 3 |
| Example 2 | 17000 | 99.4 | 64.9 | 74.4 | 50 | 3 |
| Example 3 | 23900 | 98.8 | 56.2 | 75.6 | 50 | 10 |
| Example 4 | 17300 | 94.8 | 68.1 | 79.8 | 0 | 3 |
| Example 5 | 18800 | 92.5 | 67.5 | 82.9 | 0 | 3 |
| Example 6 | 18700 | 95.6 | 62.4 | 85.6 | 0 | 3 |
| Example 7 | 23900 | 98.8 | 56.2 | 75.6 | 50 | 10 |
| Example 8 | 20400 | 99.1 | 56.2 | 85.2 | 0 | 10 |
| Example 9 | 20500 | 99.5 | 54.2 | 75.3 | 50 | 10 |

[1] mol propylene/mol Ni
[2] a ratio of 2,3-dimethyl-1-butene to total dimers products.

| | Solvent | Phosphorus compound (mmol) | | Organoaluminum oxy-compound (mmol) | | Nickel compound (mmol) | |
|---|---|---|---|---|---|---|---|
| Example 1 | Cl-Ph | Pi-Pr$_3$ | 0.10 | MAO | 2.50 | Ni(COD)$_2$ | 0.025 |
| Example 2 | Cl-Ph | Pi-Pr$_3$ | 0.10 | MAO | 2.50 | Ni(COD)$_2$ | 0.025 |
| Example 3 | Cl-Ph | Pi-Pr$_3$ | 0.10 | MAO | 2.50 | Ni(COD)$_2$ | 0.025 |
| Example 4 | Cl-Ph | Pi-Pr$_3$ | 0.025 | MAO | 2.50 | Ni(COD)$_2$ | 0.025 |
| Example 5 | Cl-Ph | Pi-Pr$_3$ | 0.10 | MAO | 2.50 | Ni(AcAc)$_2$ | 0.025 |
| Example 6 | Cl$_2$-Ph | Pi-Pr$_3$ | 0.10 | MAO | 2.50 | Ni(COD)$_2$ | 0.025 |
| Example 7 | Decane | Pi-Pr$_3$ | 0.10 | MAO | 2.50 | Ni(COD)$_2$ | 0.025 |
| Example 8 | Decane | Pi-Pr$_3$ | 0.10 | MAO | 2.50 | Ni(COD)$_2$ | 0.025 |
| Example 9 | Me-Ph | P-Cy$_3$ | 0.10 | MAO | 2.50 | Ni(COD)$_2$ | 0.025 |

Notation of chemical compounds:
Cl-Ph: chlorobenzene, Cl$_2$-Ph: o-dichlorobenzene, Pi-Pr$_3$: triisopropylphosphine, P-Cy$_3$: tricyclohexylphosphine, MAO: methylalumioxane, Ni(COD)$_2$: bis(cyclooctadienyl)nickel, Ni(AcAc)$_2$: bis-(acetylacetonato)nickel A selective trimerization of 3-methylpentene is illustrated below as an example of trimerizaiton of α-olefins.

EXAMPLE 10

Bis(cyclooctadienyl)nickel in an amount of 0.025 mmol, 0.10 mmol of triisopropylphosphine and 2.50 mmol of methylaluminoxane having a molecular weight of about 900 g/mol (a product of Sherring Co., Ltd.) were mixed and brought into contact together in toluene. The resultant catalyst was placed in a 75 ml autoclave. Ethylene was then introduced into the autoclave, and allowed to react with stirring at room temperature for 10 hours.

After completion of the reaction, the pressure in the autoclave was reduced to the normal one. The reaction products were treated with dilute hydrochloric acid, and analyzed by gas chromatography.

The analysis showed that a conversion of ethylene was 95.4%, an activity was 14900 mmol ethylene/mmol Ni, a C$_6$ fraction was obtained in an amount of 46.9% and a selectivity of 3-methylpentene in the C$_6$ fraction was 95.1%.

What is claimed is:

1. An oligomerization catalyst for α-olefins, comprising
   [A] at least one nickel compound selected from the group consisting of a nickel salt of organic acid, a nickel salt of inorganic acid and a complex compound of nickel,

[B] an organoaluminum oxy-compound having at least 3 aluminum atoms in the molecule, and

[C] a trivalent phosphorous compound represented by the formula [I]

$$PR^1R^2R^3 \qquad [I]$$

wherein $R^1$, $R^2$ and $R^{hu}$ are each independently a hydrocarbon group or substituted hydrocarbon group having 1 to 10 carbon atoms.

2. The oligomerization catalyst according to claim 1 wherein the nickel compound is bis(cyclooctadienyl)-nickel.

3. The oligomerization catalyst according to claim 1 wherein the trivalent phosphorous compound is triisopropylphosphine.

4. The oligomerization catalyst according to claim 1 wherein the molecular ratio ((A)/B) of the component (A) to the catalyst component (B) in terms of aluminum atom is in the range of 100 to 1/10,000.

5. The oligomerization catalyst according to claim 1 wherein the molecular ratio of ((C)/(B)) of the catalyst component (C) to the catalyst component (B) in terms of aluminum atom in the range of 400 to 4/10,000.

6. The oligomerization catalyst according to claim 1, wherein the organoaluminum oxy-compound is an aluminoxane.

7. The oligomerization catalyst according to claim 1, wherein the organoaluminum oxy-compound is a benzene insoluble organoaluminum oxy-compound.

8. The oligomerization catalyst according to claim 7, wherein said benzene-insoluble organoaluminum oxy-compound comprises an alkyloxyaluminum unit (i) represented by formula (III)

wherein $R^4$ is a hydrocarbon group of from 1 to 12 carbon atoms.

9. The oligomerization catalyst according to claim 1, wherein the organoaluminum oxy-compound (B) has from 3 to 50 aluminum atoms.

10. The oligomerization catalyst according to claim 1, wherein the $R^1$, $R^2$, and $R^3$ of the trivalent phosphorous compound (C) are each independently, an alkyl group, a cycloalkyl group, an aryl group, aralkyl group, or an alkoxy group.

11. The oligomerization catalyst according to claim 4, wherein the mole ratio (C)/(B) of the catalyst (C) to the catalyst component (B) in terms of aluminum atom is in the range of 400 to 4/10,000.

12. The oligomerization catalyst according to claim 3, wherein the nickel compound is bis-cyclooctadienyl) nickel.

* * * * *